United States Patent [19]
Che et al.

[11] Patent Number: 6,026,329
[45] Date of Patent: Feb. 15, 2000

[54] SKIN CARE MACHINE USING MICRO CURRENT

[75] Inventors: Tae Young Che, Seoul; Si Chel Lee, Anshan; Jae Woo Han, Kunpo; Jong In Jeung, Anyang; Jae Aog An, Uiwang, all of Rep. of Korea

[73] Assignee: Sein Electronics Co., Ltd., Rep. of Korea

[21] Appl. No.: 09/225,797

[22] Filed: Jan. 5, 1999

[30] Foreign Application Priority Data

Oct. 1, 1998 [KR] Rep. of Korea .......................... 98 184

[51] Int. Cl.$^7$ ...................................................... A61N 1/18
[52] U.S. Cl. ............................................................ 607/64
[58] Field of Search .................................. 607/59, 62, 63, 607/64

[56] References Cited

U.S. PATENT DOCUMENTS

| | | | |
|---|---|---|---|
| 4,738,250 | 4/1988 | Fulkerson et al. | 607/63 |
| 5,285,781 | 2/1994 | Brodard | 607/59 |

Primary Examiner—William Kamm
Attorney, Agent, or Firm—Galgano & Burke

[57] ABSTRACT

The disclosure is a skin care machine having a constant current generating function and giving a skin bounce thereof and soft by applying a micro constant current to the skin, and including a memory storing a guide picture including a process applying the constant current to the skin of respective body parts with an electric conductive material as a body part and a picture thereof; a graphic display unit displaying a guide picture including a process applying the constant current to the skin of respective body parts with the electric conductive material as the body part and the picture thereof stored in the memory; and a controlling unit transmitting a guide picture including a process applying the constant current to the skin of respective body parts with the electric conductive material as the body part and the picture thereof stored in the memory to the graphic display unit, as a given process. Further, the aforesaid skin care machine using a micro current can gives skin its bounce and soft by transmitting a very small current having a size similar to a biological current through an electric conductive material to the skin of a body in a uniform size to stretch or relax the skin muscle, and also can select a proper current, frequency, waveform, polarity and using time, etc., in a rapid method through a communication method with a graphic displaying function.

5 Claims, 9 Drawing Sheets

SKIN CARE MACHINE USING MICRO CURRENT

BACKGROUND OF THE INVENTION

1. Field of the Invention

The present invention relates to a skin care machine using a micro current, and more particularly to a skin care machine using the micro current capable of offering skin its bounce and soft by transmitting a very small current having a size similar to a biological current through an electric conductive material to the skin of a body in a uniform size to stretch or relax the skin muscle.

2. Discussion of Related Art

In general skin massage, there is methods using cosmetics and far infrared rays, etc., besides a method using a man's power such as a finger pressure therapy, message and so on. Currently, since it has an excellent effect to a skin message method using a micro current capable of giving skin its bounce and soft by transmitting a very small current having a size similar to a biological current through an electric conductive material to the skin of a body in a uniform size to stretch or relax the skin muscle, the message method using the micro current as mentioned above is being steadily studied. Accordingly, the skin care machine using this method has been used by skin care experts in many skin beauty shops for thirty years or more. In case of steadily using such skin care machine daily for seven to eight weeks, the user obtains much excellent effect in giving skin its bounce compared with a method using cosmetics or other skin care machines. Further, after steadily using this machine daily for seven to eight weeks, the user can always maintain his skin's bounce only by using it one a week.

The conventional skin massage machine using the micro current is using a micro constant current output function of constantly controlling an output current to be selected in 剳 unit even when an impedance of an output is changed; a current selecting function capable of selecting one of various currents of 剳 unit as a current of an output waveform; a frequency selecting function selecting one of various frequencies of Hz unit as a frequency of the output waveform; a waveform selecting function of selecting output waveform of various forms having different gradients; a polarity selecting function of selecting a polarity of the output waveform in a positive current, negative current or an alternating current of a positive pole and negative pole: a timer function of controlling an operation to be automatically stoped if the set times according to use parts has passed; an output display function for automatically stopping an operation in a sate that lines are cut off or not connected by displaying a lapse of the time to be output for a required entire output; a display function of displaying details of an output current, output frequency, a use time and use mode, etc., and a use part; a dry cell exchange time alarming function of informing a user of the exchange time when a life of the dry cell is expired; and an automatic power cut-off function for reducing an unnecessary consumption of the dry cell by automatically cutting off the power when a given time period has lapsed in no use state.

However, the aforesaid conventional skin message machine using the micro current displays only characters to the user and therefor, the general users have difficulty in using it. It is because that the above skin message machine has many parts to be set through special information. That is, this is because that proper current, frequency, waveform, polarity and use time, etc., have to be properly selected to be used according to complex skin parts so as to maximize an effect for continuously maintaining the skin's bounce after the user improves his skin's bounce, and since the message direction and method are different according to each part of the body, the general users without special information of the skin care can not easily understand a setting method. Moreover, it is not also easy for skin care experts to rapidly manipulate the machine only with the simply displayed characters. Accordingly, though the general users wants to use the skin care machine using the micro current for their skin care, because it is very difficult to learn the using method of the machine, they unwilling use the skin beauty shop in spite of its expensive service charge. As mentioned above, the conventional skin care machine with the micro current has a disadvantage not to be easily used at home due to its difficult using method.

SUMMARY OF THE INVENTION

Accordingly, the present invention is directed to a skin care machine using a micro current that substantially obviates one or more of the problems due to limitations and disadvantages of the related art.

An object of the present invention is to provide a skin care machine using a micro current capable of selecting a proper current, frequency, waveform, polarity and using time, etc., in a rapid method for the many kinds of skin messages through a communication method by add a graphic display function to a small portable skin care machine using a micro computer, and also capable of observing skin parts displayed by a graphic and a special skin care method such as a using method of a probe or carbon pad and a message direction through the graphic, thereby being easily used by the user.

Another object of the present invention is to provide a skin care machine using a micro current capable of being manipulated through the manipulation method by the graphic display without a using manual by displaying a proper manipulation method of a prober carbon pad, etc., by the graphic according to each massage part for a wide skin.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a skin care machine having a constant current generating function and giving a skin bounce thereof and soft by applying a micro constant current to the skin, comprises: a memory storing a guide picture including a process applying the constant current to the skin of respective body parts with an electric conductive material as a body part and a picture thereof; a graphic display unit displaying a guide picture including a process applying the constant current to the skin of respective body parts with the electric conductive material as the body part and the picture thereof stored in the memory; and a controlling unit transmitting a guide picture including a process applying the constant current to the skin of respective body parts with the electric conductive material as the body part and the picture thereof stored in the memory to the graphic display unit, as a given process. Further, aforesaid machine includes: a key input unit generating a key signal by a user; a detecting unit detecting whether said electric conductive material is contacted to the skin or not, and changing it to an electric signal to output the electric signal; and a buzzer generating a buzzer tone according to a control signal when a guide picture including a process applying the constant current to the skin of respective body parts with an electric conductive material as a body part and a picture thereof displayed in said graphic display unit is changed to a next guide picture and a next body picture is displayed.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the invention:

DETAILED DESCRIPTION OF PREFERRED EMBODIMENT

Reference will now be made in detail to the preferred embodiments of the present invention, examples of which are illustrated in the accompanying drawings.

Figure 1:
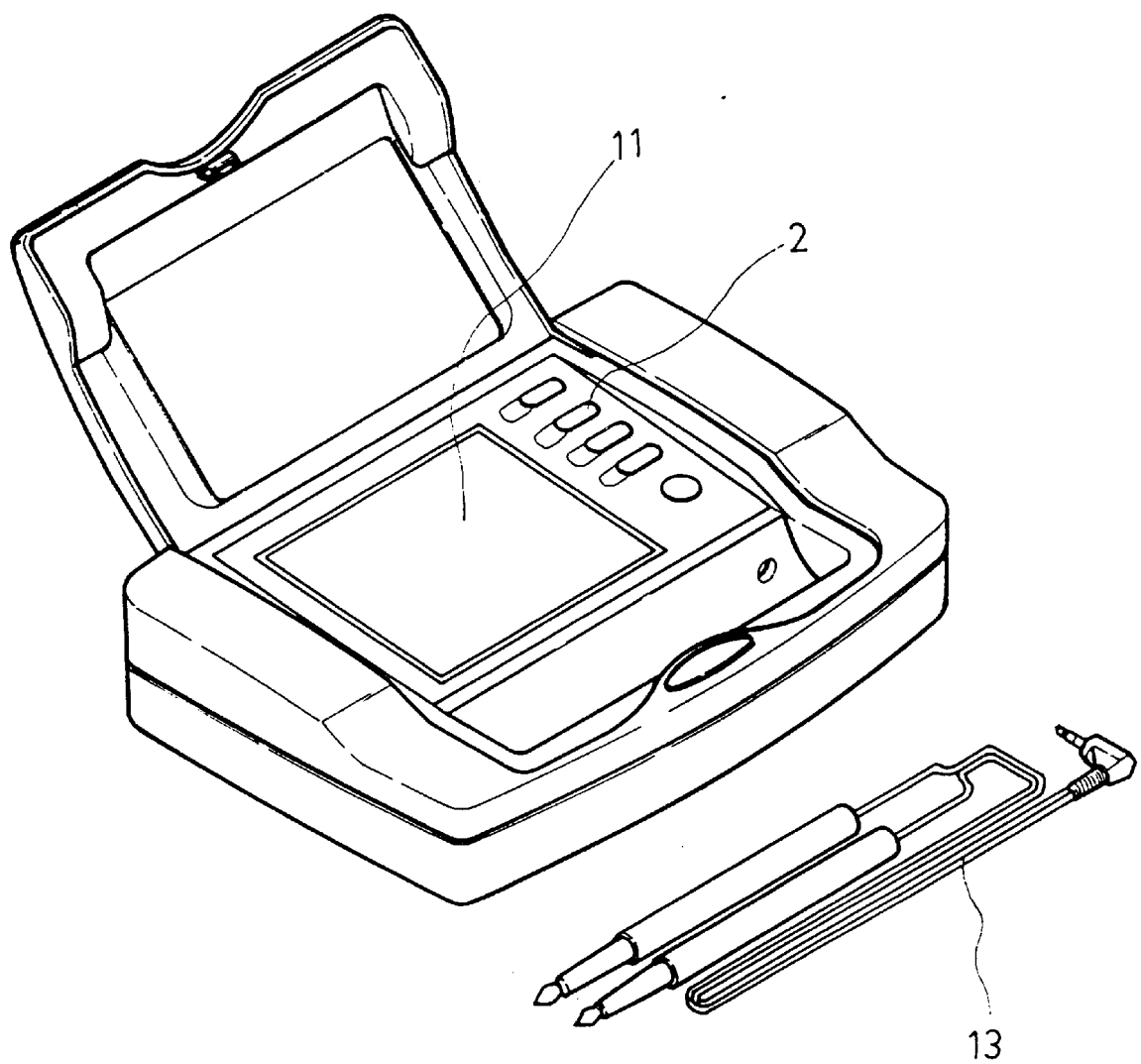
FIG. 1 is a perspective view of a skin care machine using a micro current in accordance with an embodiment of the present invention.
Figure 2:
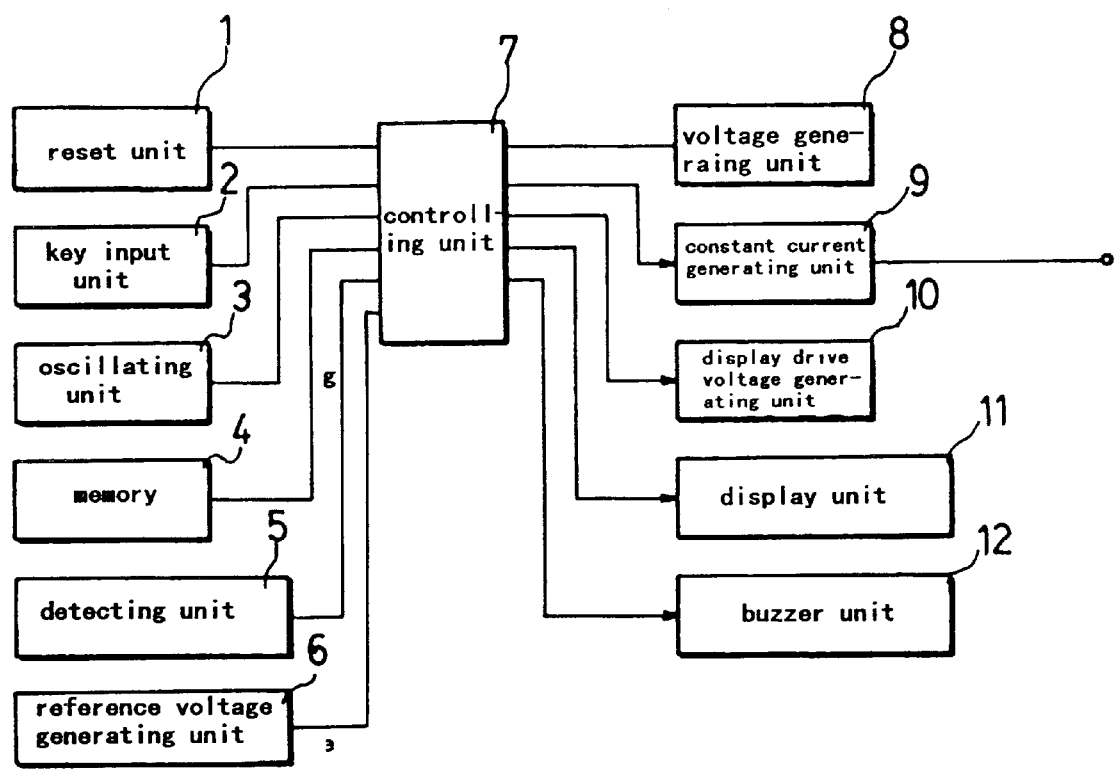
FIG. 2 is a block diagram of the skin care machine using the micro current in accordance with the embodiment of the present invention.
Figure 3:
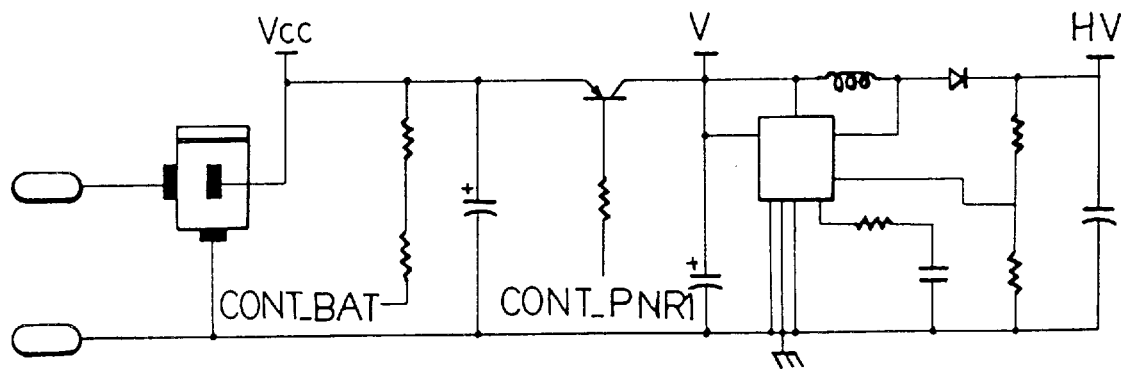
FIG. 3 is a detail circuit diagram of a voltage generating unit of the skin care machine using the micro current in accordance with the embodiment of the present invention.
Figure 4:
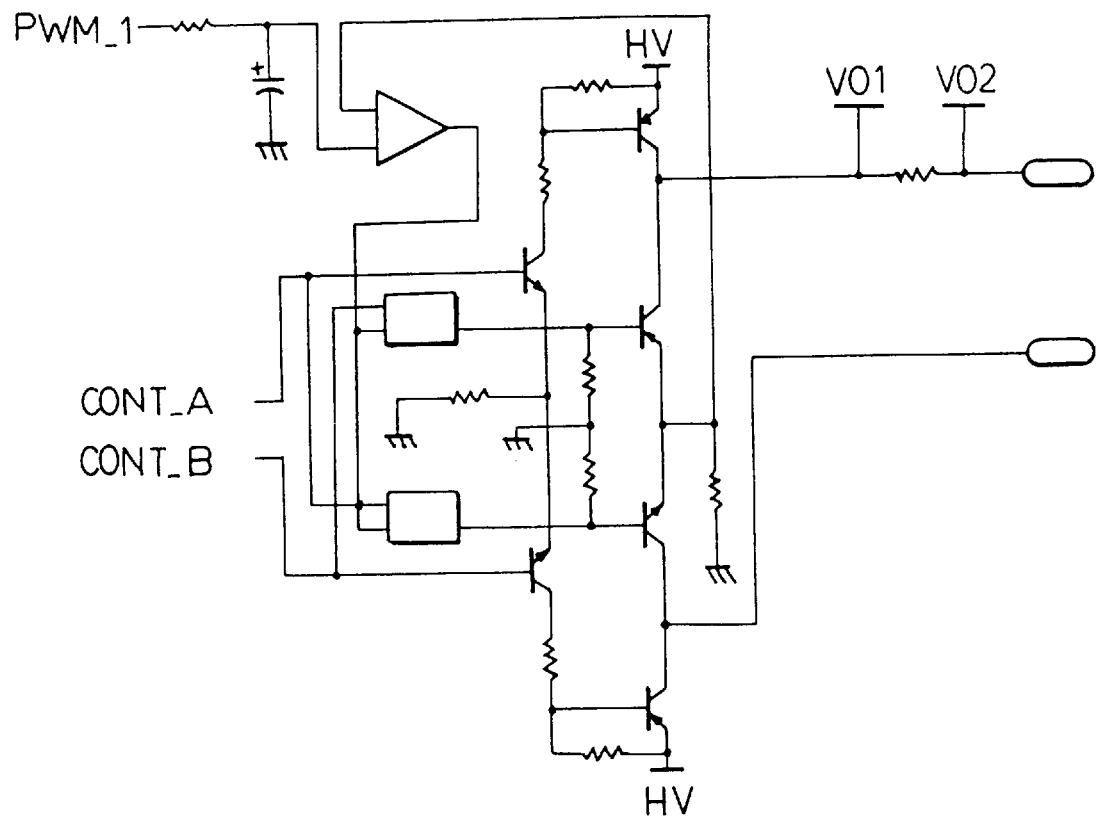
FIG. 4 is a detail circuit diagram of a constant current generating unit of the skin care machine using the micro current in accordance with the embodiment of the present invention.
Figure 5:
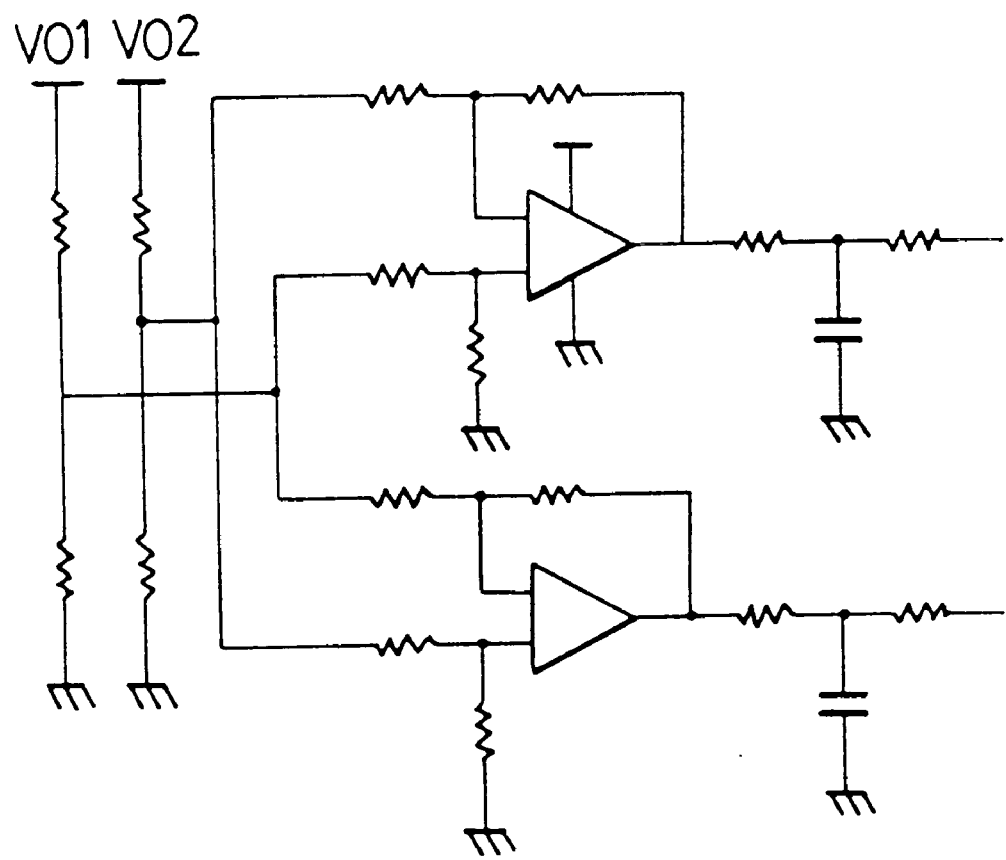
FIG. 5 is a detail circuit diagram of a detecting unit of the skin care machine using the micro current in accordance with the embodiment of the present invention.

In FIGS. 1 and 2, a skin care machine using a micro current in accordance with an embodiment of the present invention is comprised of: a reset unit 1 generating a reset signal when a power is applied; a key input unit 2 generating a key signal by a user; an oscillating unit 3 generating an oscillation signal to output it; a memory 4 storing graphic data and program; a detecting unit 5 detecting whether an electric conductive material is contacted to a body or not; a reference voltage generating unit 6 generating a reference voltage; a controlling unit 7 generating a control signal with signals input from the reset unit 1, the key input unit 2, the oscillating unit 3, the memory 4, the detecting unit 5 and the reference voltage unit 6; a voltage generating unit 8 generating a voltage to output it; a constant current generating unit 9 generating a constant current with the voltage to output it; a graphic display drive voltage generating unit 10 generating a voltage for driving a graphic display unit 11; the graphic display unit 11 for a user interface; and a buzzer 12 generating a buzzer tone.

Hereinafter, the operation of the skin care machine using the micro current in accordance with an embodiment of the present invention will be described with reference to FIGS. 6 to 9.

Figure 6:
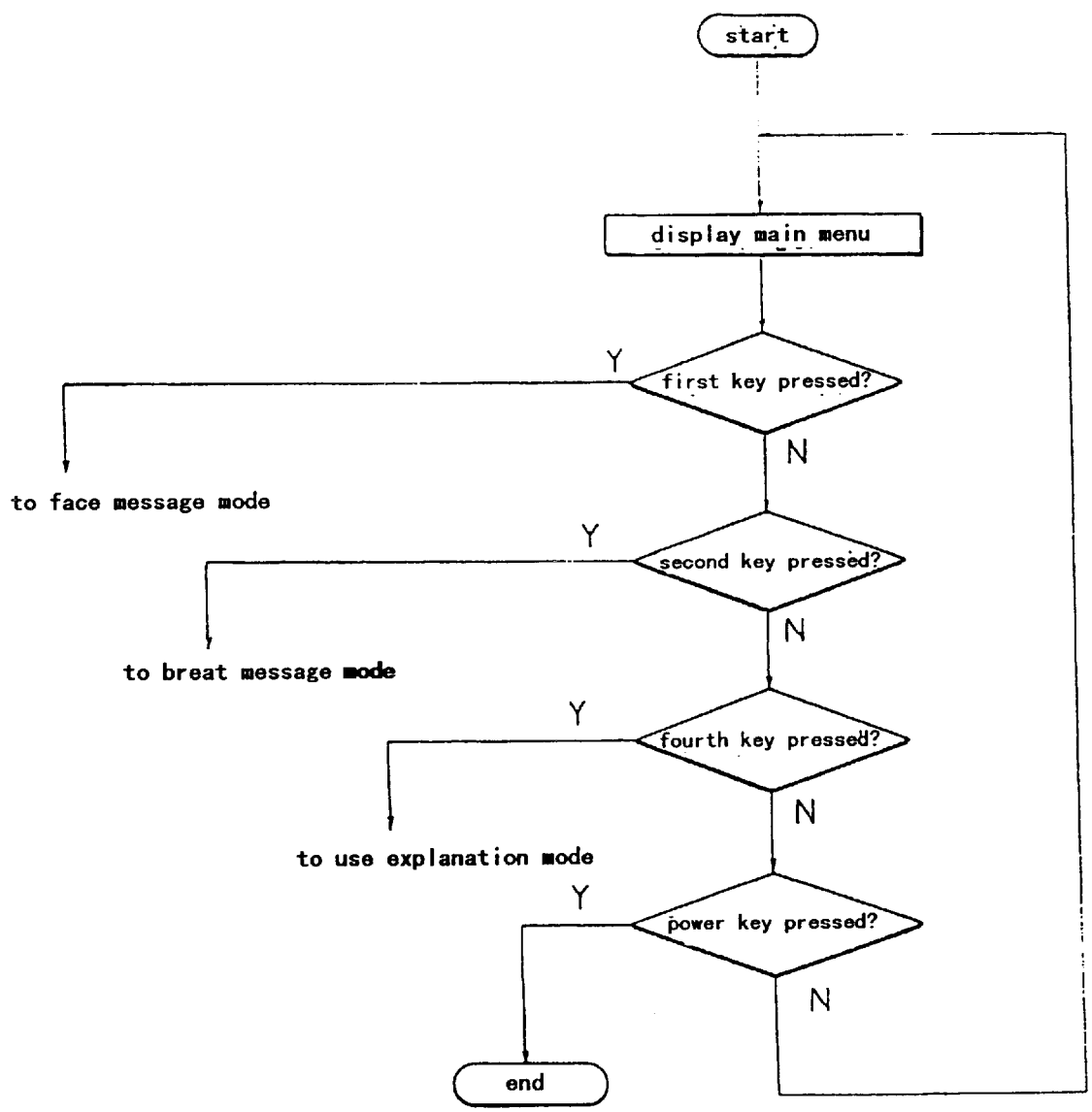
FIG. 6 is a flow chart of a main control program of the skin care machine using the micro current in accordance with the embodiment of the present invention.

If the power is supplied as the user presses the power key of the key input unit 2, the controlling unit 7 performs operations programmed in the memory 4 as shown in FIGS. 6 to 9 and thereby, the skin care machine starts to operate. The key input unit 2 comprises one power key and four menu selecting keys and as seen in FIG. 6, once the operation is started, a main menu is displayed on a screen of the graphic display unit 11. The most important characteristic of the present invention is to have a convenient function of a menu method using the graphic display unit 11. In the this main menu, the first key is for a face message, the second key for a breast message and the fourth key for an explanation of a usage. In each function, the user can practice the function by pressing a numeral key corresponding to detail to be desired or manipulating an electric conductive material 13.

Figure 7:
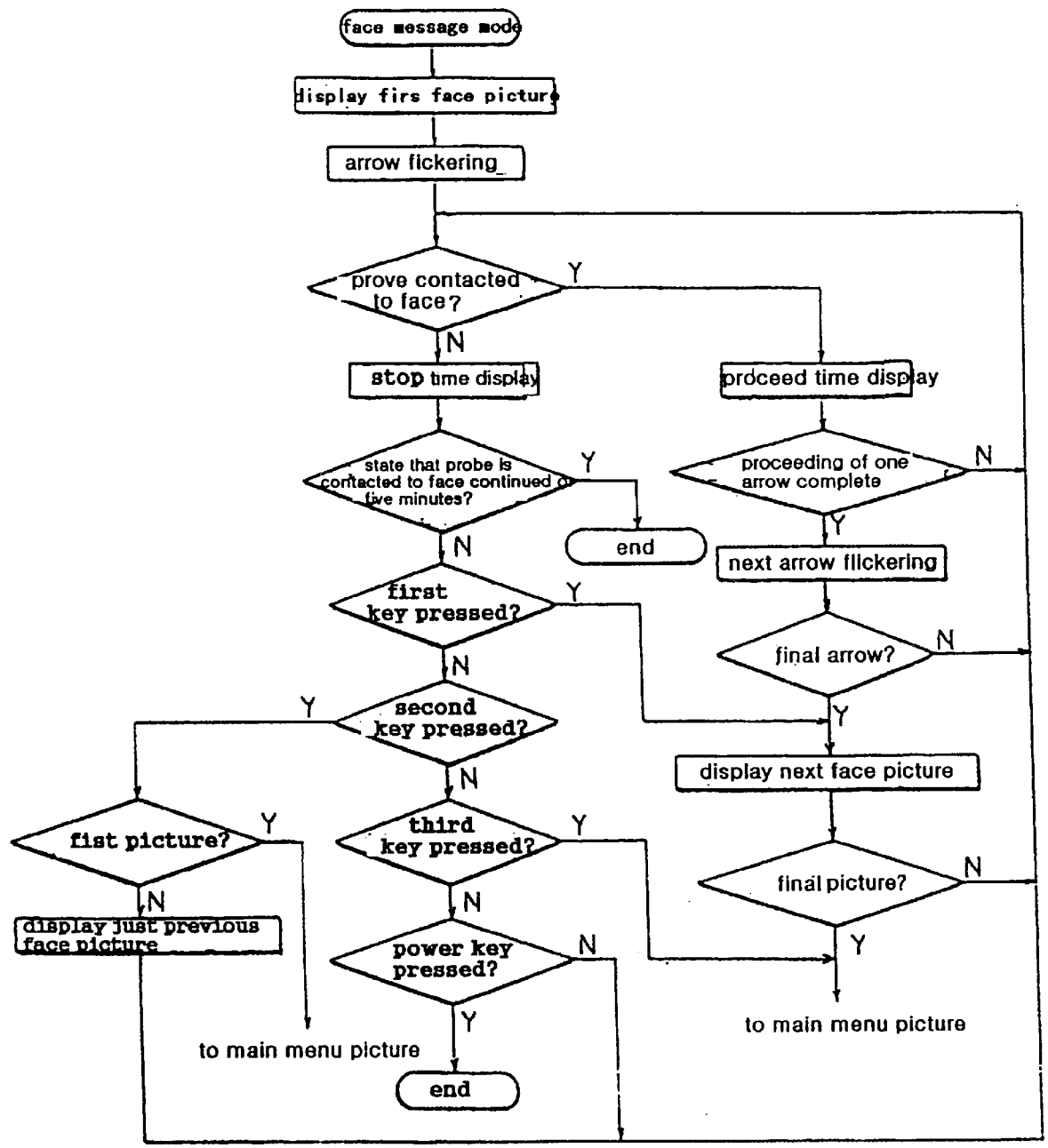
FIG. 7 is a flow chart of a face massage mode sub program of the skin care machine using the micro current in accordance with the embodiment of the present invention.

In the main menu, if the user presses the first key, the face massage mode is performed shown in FIG. 7. If the face message mode is started, the face is displayed on the screen of the graphic display unit 11 as seen in FIG. 19, and, an arrow indicating a position and direction of the face skin to be massaged are sequently displayed for a given time period. Accordingly, the user moves the electric conductive material on the face along the arrow for a given time period as indicated on the picture or contacts it to the face, thereby performing the message. The usage of the electric conductive material 13 is served in the use explanation mode. In the face massage mode, in case that the user wants to start massaging from a special part of the face, if the user repeatedly presses the first key until the desired part has been displayed, the user can start massaging from the desired part. Further, in case that the user wants to massage the preceding part again, the user has to repeatedly press the second key until the desired part has been displayed. And, in case that the user wants to stop massaging in a middle step, the user has to press the third key for returning to the main picture.

Figure 8:
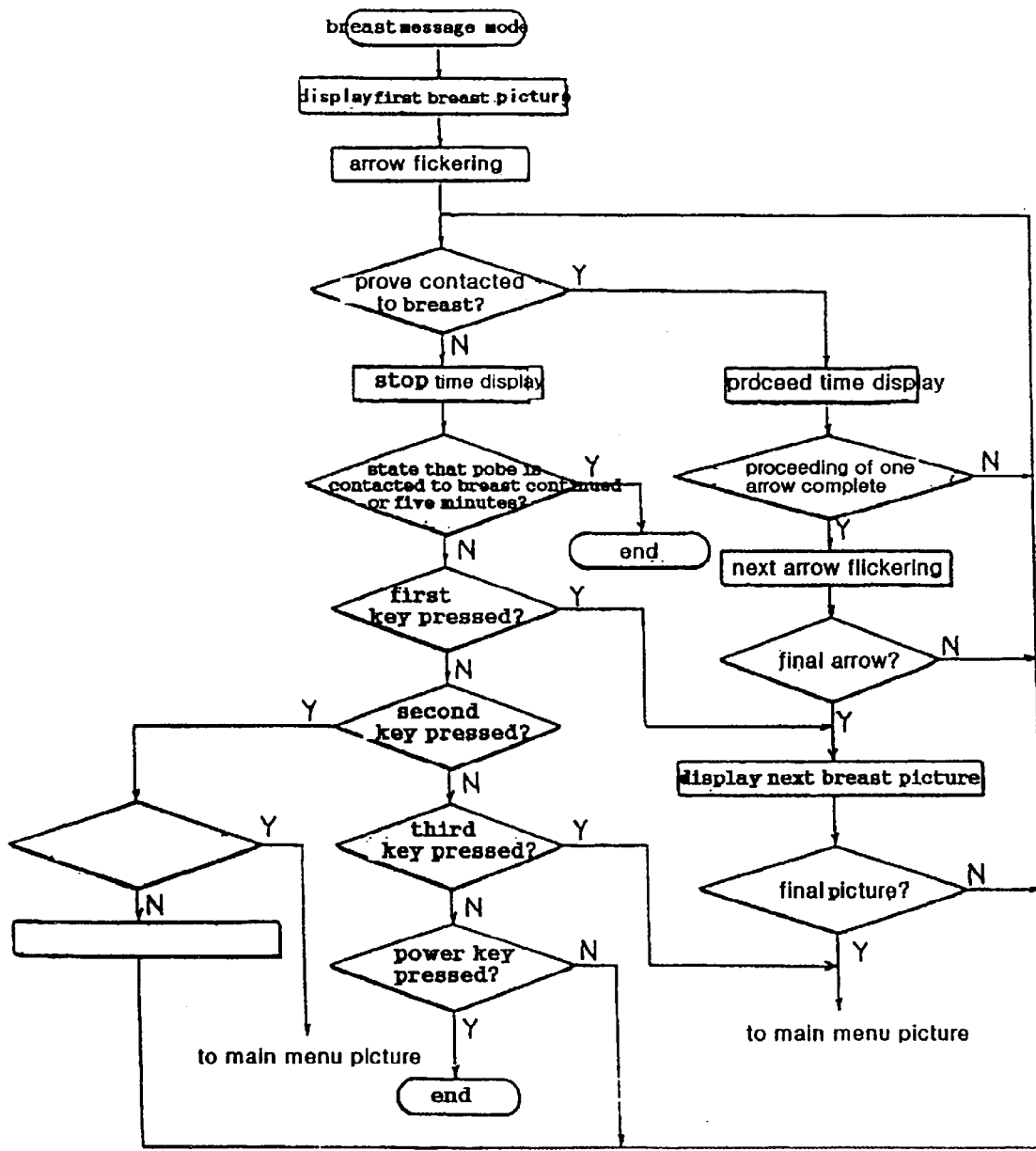
FIG. 8 is a flow chart of a breast massage mode sub program of the skin care machine using the micro current in accordance with the embodiment of the present invention.

If the user presses the second key in the main menu, the breast massage mode proceeds as shown in FIG. 8. However, the breast massage mode proceeds in the same steps as the face massage mode and therefor, a detailed explanation thereof will be avoided.

In the face massage mode, the massage for twenty tow face parts automatically proceeds twice and on the other hand, in the breast massage mode, the message for the twelve breast parts automatically proceeds twice. Whenever the message for each part, the present step is displayed in the graphic display unit 11, and the residual message time is also displayed therein, and the proceeding time of one arrow is displayed as an asterisk mark. The residual time and the arrow proceeding mark is shown when the electric conductive material 13 is contacted to the face or the breast and if it is removed from the face or the breast, they are disappeared.

Figure 9:
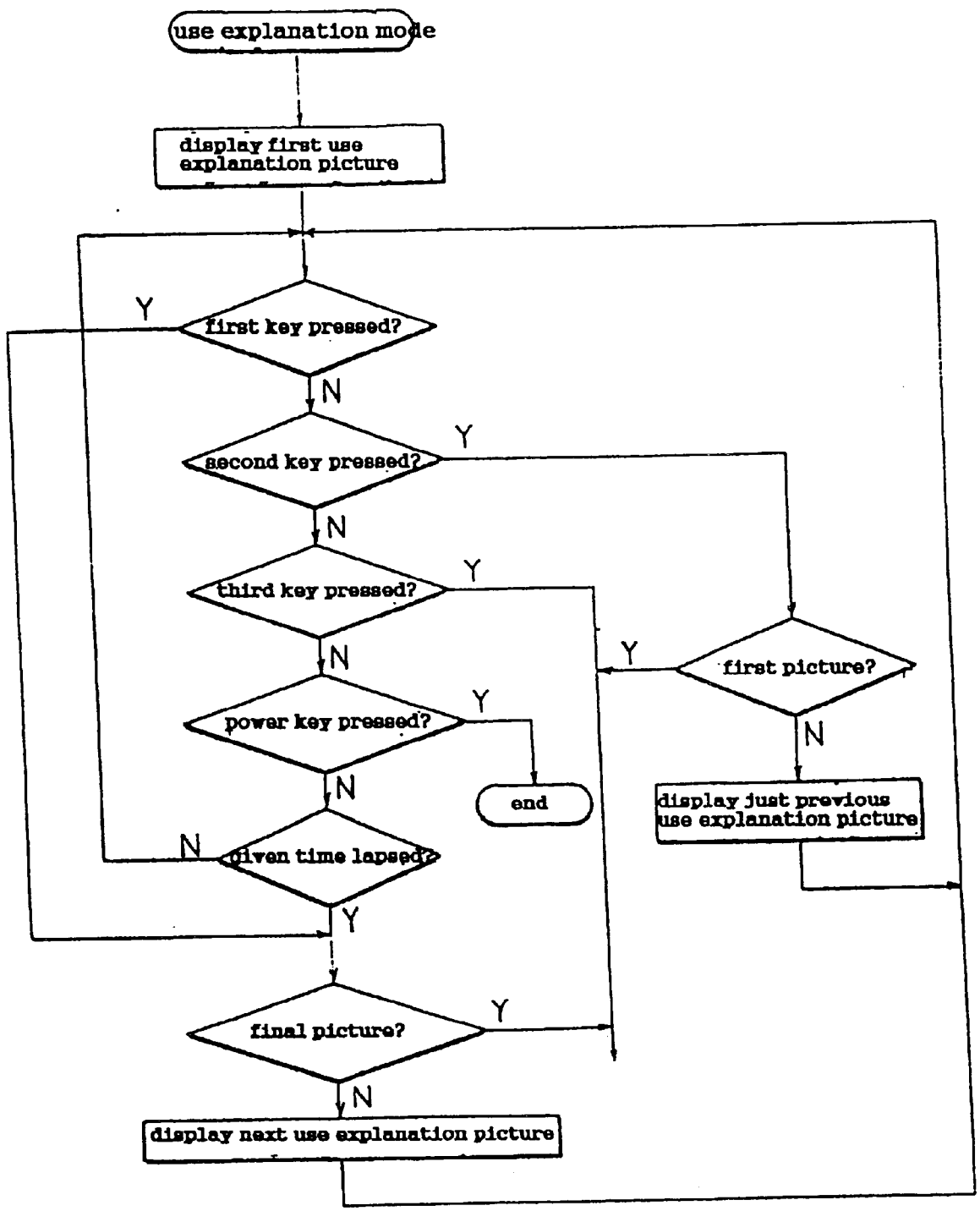
FIG. 9 is a flow chart of a use explanation mode sub program of the skin care machine using the micro current in accordance with the embodiment of the present invention.
Figure 10:
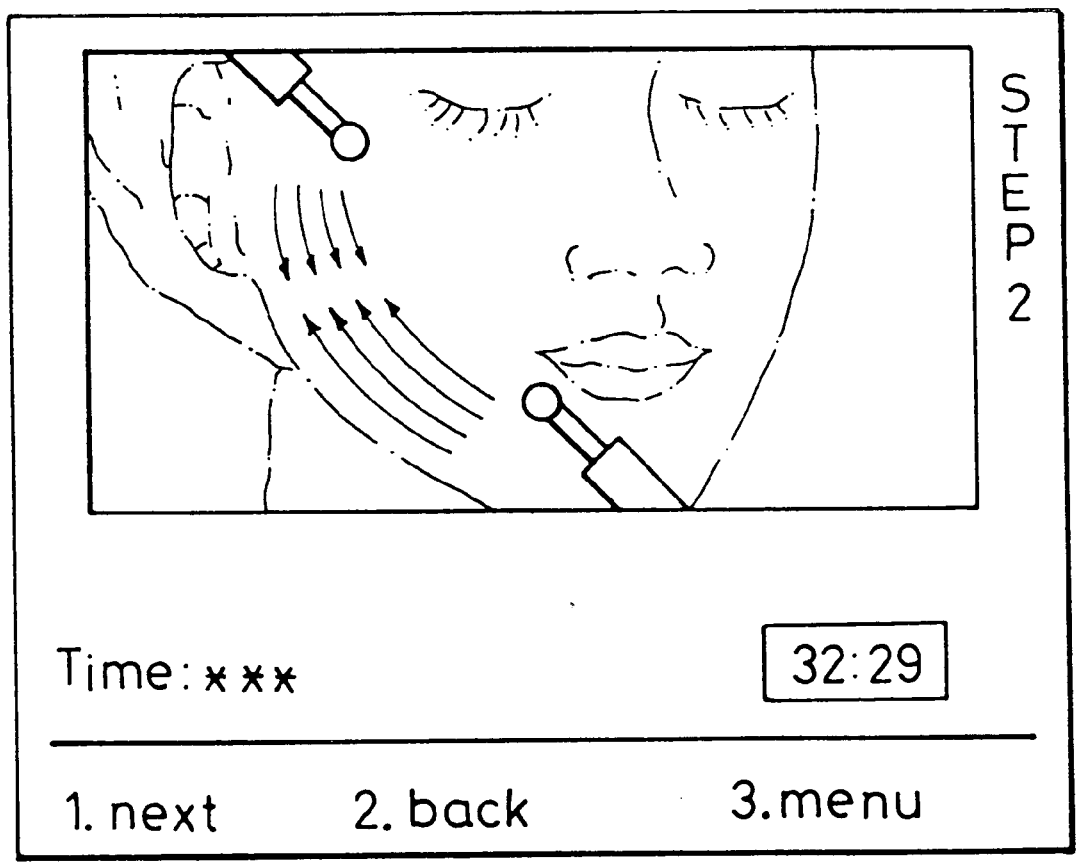
FIG. 10 is a view showing a use picture of the skin care machine using the micro current in accordance with the embodiment of the present invention.

If the user presses the fourth key in the main menu, the use explanation mode proceeds shown in FIG. 9, and then the usage explanation is displayed in the graphic display unit 11 as the key manipulation.

Meanwhile, if the detecting unit 5 senses that the electric conductive material 13 is contacted to the face, the controlling unit 7 outputs the control signal CONT-PWR1 to the voltage generating unit 8 and then, the voltage from the voltage generating unit 8 is applied to the constant current generating unit 9. If the voltage is applied, the constant current generating unit 9 outputs the constant current by pulse signals output from the controlling unit 7 and, a positive and negative constant current output flows to the final output terminal of the constant current generating unit 9 according pulse signals CONT-A and CONT-B output from the controlling unit 7.

The reference voltage generated from the reference voltage generating unit 6 is used as the reference voltage upon operation of the controlling unit 7, and is applied to a DC/DC converter of the graphic display drive voltage generating unit 10 and then, the graphic display drive voltage is generated to be output to the graphic display unit 11. The graphic display drive voltage generating unit 10 amplifies DC 6 V voltage to AC 100 V voltage with an inverter to drive a back light of the graphic display unit 11.

The detecting unit 5 connected to the output terminal of the constant current generating unit 9 checks voltages of both terminal of a resistor connected in series to the output terminals thereof, thereby detecting whether the electric conductive material becomes ON or OFF, and if the output current more than a regulated current is provided, serves as a safety machine stopping the output of the controlling unit 7.

The graphic display unit 11 uses a graphic light emitting diode LCD where an electroluminescence EL backlight is buried, displays the part to be massaged with the arrow in the face and breast massage modes, respectively displays twenty tow face pictures in each of the first and second steps, and respectively displays twenty two breast pictures in each of the first and second steps, under a control of the controlling unit 7.

When the arrow displayed on the picture of the graphic display unit 11 proceeds next and the picture is changed to the next picture, the buzzer 12 generates a buzzer tone.

The controlling unit 7 has an auto power-off function automatically cutting off the power if a given time has lapsed after the proceeding stops, and a function checking the battery voltage.

In discussed previously, a skin care machine using a micro current can offer skin its bounce and soft by transmitting a very small current having a size similar to a biological current through an electric conductive material to the skin of a body in a uniform size to stretch or relax the skin muscle, and also can select a proper current, frequency, waveform, polarity and use time, etc., in a rapid method through a communication method with a graphic displaying function.

It will be apparent to those skilled in the art that various modifications and variations can be made in a skin care machine using a micro current of the present invention without departing from the spirit or scope of the invention. Thus, it is intended that the present invention cover the modifications and variations of this invention provided they come within the scope of the appended claims and their equivalents.

What is claimed is:

1. A skin care machine having a constant current generating function and giving a skin bounce thereof and soft by applying a micro constant current to the skin, said machine comprising:

a memory storing a guide picture including a process applying the constant current to the skin of respective body parts with an electric conductive material as a body part and a picture thereof;

a graphic display unit displaying a guide picture including a process applying the constant current to the skin of respective body parts with said electric conductive material as the body part and the picture thereof stored in said memory; and a controlling unit transmitting a guide picture including a process applying the constant current to the skin of respective body parts with said electric conductive material as the body part and the picture thereof stored in said memory to said graphic display unit, as a given process.

2. A machine as claimed in claim 1 comprising a key input unit generating a key signal by a user.

3. A machine as claimed in claim 2 comprising a detecting unit detecting whether said electric conductive material is contacted to the skin or not, and changing it to an electric signal to output the electric signal.

4. A machine as claimed in claim 2 comprising a buzzer generating a buzzer tone according to a control signal when a guide picture including a process applying the constant current to the skin of respective body parts with an electric conductive material as a body part and a picture thereof displayed in said graphic display unit is changed to a next guide picture and a next body picture is displayed.

5. A machine as claimed in claim 2, wherein said controlling unit generates a control signal for an auto power-off function automatically cutting off the power if a given time period has lapsed after the proceeding is stoped and a function checking a battery voltage.

* * * * *